(12) United States Patent
Stöcker et al.

(10) Patent No.: US 8,557,605 B2
(45) Date of Patent: Oct. 15, 2013

(54) ANALYZING METHODS AND DEVICES FOR BIOLOGICAL REACTIONS BETWEEN A LIQUID PHASE AND A SOLID PHASE

(75) Inventors: Winfried Stöcker, Groß Grönau (DE); Martin Rateike, Pansdorf (DE); Bianca Maltzahn, Groß Sarau (DE); Rasmus Behring, Lübeck (DE)

(73) Assignee: Euroimmun Medizinische Labordiagnostika AG, Lubeck (DE)

( * ) Notice: Subject to any disclaimer, the term of this patent is extended or adjusted under 35 U.S.C. 154(b) by 513 days.

(21) Appl. No.: 12/622,279

(22) Filed: Nov. 19, 2009

(65) Prior Publication Data
US 2010/0124750 A1    May 20, 2010

(30) Foreign Application Priority Data
Nov. 19, 2008    (EP) .................................... 08169465

(51) Int. Cl.
*G01N 33/558*    (2006.01)
(52) U.S. Cl.
USPC ......................................................... 436/514
(58) Field of Classification Search
None
See application file for complete search history.

(56) References Cited

U.S. PATENT DOCUMENTS

| 4,339,241 | A |   | 7/1982  | Stöcker ...................... 23/230 B |
|-----------|---|---|---------|---------------------------------------|
| 4,422,386 | A | * | 12/1983 | Carpenter ................... 109/59 R |
| 4,647,543 | A | * | 3/1987  | Stocker ....................... 436/174 |
| 5,741,647 | A | * | 4/1998  | Tam ............................ 435/6.11 |
| 5,756,304 | A | * | 5/1998  | Jovanovich ..................... 435/34 |

(Continued)

FOREIGN PATENT DOCUMENTS

| DE | 202 15 270 | 2/2003 |
| DE | 202 15 268 | 5/2003 |

(Continued)

OTHER PUBLICATIONS

BAMA FDA manual, published 2001.*

(Continued)

*Primary Examiner* — N. C. Yang
*Assistant Examiner* — Richard Moerschell
(74) *Attorney, Agent, or Firm* — Seed IP Law Group PLLC

(57) ABSTRACT

The invention relates to a device for performing immunological, histochemical and cytochemical, molecular biological, enzymological, clinical-chemical and other analyzes, wherein the device comprises an object holder having one or more elongate adhesive surfaces and a reagent holder having one or several channels. The object holder is detachably connectable to the reagent holder in such a manner that the elongate adhesive surfaces each face one of the channels and, when reaction partners bound to a solid phase are disposed on the elongate adhesive surfaces and reactants dissolved in liquid are present in the channels, the reaction partners and the reactants are in contact. Means are provided for preventing the liquid from passing from one channel into an adjacent channel. A method for performing a corresponding analysis can be performed with this device, by connecting the object holder to the reagent holder in such a manner that the elongate adhesive surfaces each face a channel, liquid having reactants dissolved therein is introduced into the channels such that the solid phase substrates having reaction partners bound thereto and being disposed on the adhesive surfaces come into contact with the liquid, and the object holder and the reagent holder are moved together in such a manner that the liquid alternately moves into the two longitudinal directions of the channels.

19 Claims, 5 Drawing Sheets

(56) References Cited

U.S. PATENT DOCUMENTS

| | | | |
|---|---|---|---|
| 6,369,252 B1* | 4/2002 | Akoh | 554/227 |
| 2003/0072685 A1* | 4/2003 | Goldman et al. | 422/102 |
| 2005/0196318 A1 | 9/2005 | Matusewicz et al. | 422/58 |
| 2007/0141049 A1* | 6/2007 | Bredehorst et al. | 424/133.1 |
| 2007/0237687 A1 | 10/2007 | Sleeper | 422/104 |

FOREIGN PATENT DOCUMENTS

| | | |
|---|---|---|
| EP | 0 075 605 | 4/1983 |
| EP | 1 415 715 | 5/2004 |
| EP | 1 559 740 | 8/2005 |
| WO | 00/39587 | 7/2000 |
| WO | 2007/140889 | 12/2007 |

OTHER PUBLICATIONS

Corning costar product 4878.*

Sigma replica plater product R2383.*

Pfeiffer, T. et al., "Diagnostic Microarray Assay for SNP-Typing of the Gene Encoding the Drug Metabolising Enzyme Arylamine N-Acetyl Transferase 2 (NAT2)," *Statusseminar Chiptechnologien, Microarray-Anwendungen in Grundlagenforschung und Routinebetrieb*, Feb. 1-2, 2007, DECHEMA-Haus, Frankfurt am Main.

Stöcker, Von W., "Rationelle Histochemie mit einer neuen Mikroanalysemethode," *Acta Histochemica, Suppl.-Band XXXI*, S:269-281, 1985.

Stöcker, W. et al., "Histochemical Screening of Monoclonal Antibodies Against Tumor- and other Antigens," *Verh. Dtsch. Ges. Path.* 70:393-395, 1986 (Summary in English).

Stöcker, W. et al., "Autoimmunity to Pancreatic Juice in Crohn's Disease, Results of an Autoantibody Screening in Patients with Chronic Inflammatory Bowel Disease," *Scand. J. Gastroenterol.* 22 (suppl. 139):41-52, 1987.

Stöcker, W. et al., "Detection of autoantibodies in clinical routine diagnosis by means of a new rational method in the field of fluorescent antibody technique," In: Schatz, H., Doniach, D. (Eds.): *Autoimmunität bei Schilddrüsenerkrankungen*. George-Thieme-Verlag Stuttgart, pp. 157-174, 1984 (Summary in English).

* cited by examiner

DETAIL D

ANALYZING METHODS AND DEVICES FOR BIOLOGICAL REACTIONS BETWEEN A LIQUID PHASE AND A SOLID PHASE

The present invention relates to specific methods and devices for performing immunological, histochemical and cytochemical, molecular biological, enzymological, clinical-chemical and other analyses, for example in medical laboratory diagnostics, wherein reaction partners bound to a solid phase are incubated with reactants dissolved in liquids. To this end, solid phase substrates are arranged on elongate adhesive surfaces of an object holder and contacted with the liquids which are present in channels—exactly opposite the adhesive surfaces—of a reagent holder, particular embodiments involving forcing turbulent convection of the dissolved reaction partners in the liquid for mixing the reactants during the incubation: the reactions proceed more rapidly, the signals become stronger and the reactivity of each substrate becomes more homogeneous over the entire surface than can be achieved by the prior art. When a plurality of samples are analysed alongside one another, the arrangement prevents the liquids of adjacent samples from mixing with one another during the incubation. At the end of the incubation, the object holders are removed from the reagent holders and the results are evaluated. Examples of the application of the invention are antibody determination in the serum of patients with suspected autoimmune or infection disorders and allergies by indirect immunofluorescence or immunoblotting, and genotyping patient samples with the aid of microarrays.

STATE OF THE ART

For the field of use of the invention, the state of the art is illustrated by an example from medical and immunological laboratory diagnostics, the "indirect immunofluorescence test" for detecting antibodies in patient serum; see FIG. 1. The serum to be analysed, or a dilution thereof, is contacted with a substrate connected firmly to an object holder, said substrate comprising antigens corresponding to the antibodies to be determined, and incubated for a particular time. Useful substrates include, amongst others: thin sections of biological tissue, bacteria smears, cells or antigen drops applied in solution, dried or coupled. In the case of positive samples, specific antibodies of the patient serum now bind to the corresponding antigens of the substrate, for example to the DNA of the cell nuclei of a tissue section. Anti-DNA antibodies are found, inter alia, in patients with the disorder lupus erythematosus.

After the first incubation step, excess unbound antibodies are washed off with buffer solution. The substrate is now incubated for a second time, this time with a fluorescein-labelled antihuman antibody directed against human immunoglobulin (this was obtained, for example, by immunizing a goat with human immunoglobulin). In the positive case, the labelled antibodies bind in the second step to the already bound antibodies of the patient serum. In a further washing step, excess unbound antibodies are again removed. Thereafter, mounting medium is applied dropwise, a cover slip is applied and the ready-incubated substrate is examined with the fluorescence microscope. In the case of positive samples, the cell nuclei of the substrate fluoresce in green when they are irradiated in the microscope with (blue) light having a wavelength of about 488 nanometers. In the case of a negative result, the cell nuclei remain dark. The cover slip creates a smooth surface which is parallel to the substrate and lies planar thereon, which is required for a perfect image, and additionally prevents the microscope lens from coming into direct contact with the substrate. The mounting medium fills the space between the substrate and the cover slip and thus ensures a scatter-free light path; it contains substances for reducing the bleaching of the fluorescence; its pH is set to a maximum fluorescence yield.

Indirect immunofluorescence is used globally in laboratory diagnostics, in order to analyse autoantibodies or infection antibodies in millions of patient sera per year. In order to better manage the number of tests, attempts are being made to combine the operating sequences and to automate the processes. According to the general state of the art, object holders with a plurality of reaction fields are therefore being used in diagnostics laboratories for the parallel testing of several patients. This rationalization step harbours the risk that, in the event of careless handling, sera arranged next to each other merge, and the diagnosis for their neighbour on the object holder is wrongly given to some patients.

The state of the analysis technology in this field of use up to 1979 is described in EP 0 018 435 [1]. That document also discloses a new method of incubation for the indirect immunofluorescence, in which the patient sera and the reagents are not applied dropwise directly to the object holders, as was customary up to then, but to hydrophilic reaction fields of a planar reagent holder, the environment of which reaction fields is hydrophobic. The object holder contains the substrates on likewise hydrophilic reaction fields, and these are positioned above the reagent holder at a defined distance such that the substrates are immersed into the droplets associated with them, as a result of which the reactions for all fields of one object holder are started simultaneously. The number of testable serum dilutions per object holder corresponds to the number of reaction fields thereof. One of the advantages of this technology is that the droplets can no longer run into one another as easily. The droplet height is fixed and constant, and the start of the reactions is simultaneous with the placing of an object holder onto the prepipetted droplets; as a result, the reactions of different tests have better comparability with one another. Evaporation is delayed, and a far lower level of troublesome unspecific coloured deposits collect in the substrates because they sediment in the opposite direction during the incubation.

Meanwhile, the indirect immunofluorescence has been developed further by a specific fragmenting technique (EP 0 117 262) [2]: here, the substrates (for example frozen sections, seeded cells or cell smears, coupled isolated antigens and so forth) are not applied directly to object holders, but rather first to thin glass slides of thickness, for example, 0.15 mm. Thereafter, these glass slides, together with the substrates adhering thereon, are divided into fragments of any size (biochips), and it is only these which are secured to object holders—for example by adhesive bonding. The fragmenting technique is particularly suitable for the mass production of substrates because it is significantly easier and faster to prepare a somewhat larger tissue section and to divide it into small biochips than to produce many small tissue sections and to mount them directly onto object holders. The advance in productivity becomes even clearer for cell culture substrates or cell smears, or for surfaces covered with defined antigens. In addition, mosaics of any extent can be composed from different substrates, such that extensive antibody profiles can be tested with one and the same drop of a serum dilution or of the reagent solution [3, 4, 5]. The invention is now being used globally. Devices and methods for substantially automated production of such object holders are described in the European patent application PCT/EP/2005/000974 (2005) [6].

The state of the art is suffering from a fundamental imperfection, in that effective permanent convection in the liquid phase is not ensured during the incubations. The sample or reagent liquid is in direct contact with the antigen-containing structures. Corresponding antibodies present bind to the target antigens, and their concentration in the immediate environment of the antigens decreases, while high antibody concentrations are still present one or two millimeters further away. Mere diffusion does not eliminate the gradient during the test time, and the measure proposed in the cited EP 0 018 435 for generating a convection (periodic alteration of the distance between object holder and reagent holder to deform the round droplet held between the two) was by no means sufficiently effective.

OBJECT OF THE INVENTION

It was to find a way, in immunological, histochemical, molecular biological, enzymological, clinical-chemical and other analyses, for example for medical laboratory diagnostics, of incubating reaction partners bound to a solid phase with reactants dissolved in liquids, the liquid being presented to the solid phase in such a way that it cannot flow off laterally, that adjacent samples do not come into contact with one another during the incubation or during the wash cycles, and that for mixing the reactants during the incubation or for effectively washing a turbulent or strong convection can be forced in the liquid.

DESCRIPTION OF THE INVENTION

This object is achieved by a device according to claim 1 and a method according to claim 12. Preferred embodiments form the subject-matter of the respective dependent claims.

It is envisaged that a device for performing immunological, histochemical and cytochemical, molecular biological, enzymological, clinical-chemical and other analyses has an object holder having one or more elongate adhesive surfaces, for example in strip form, and a reagent holder having one or more elongate channels. The object holder can be detachably connected to the reagent holder in such a manner that each of the elongate adhesive surfaces faces or is disposed opposite one of the channels and extends parallel or essentially parallel thereto and that, when reaction partners bound to a solid phase are disposed on the elongate adhesive surfaces and reactants dissolved in liquid are present in the channels, the reaction partners and reactants are in contact. Means are provided for preventing the liquid from passing from one channel to an adjacent channel. It is preferred that the object holder and the reagent holder have means which can achieve a defined position of the object holder and the reagent holder relative to one another in the connected state, i.e. a defined lateral position and/or a defined distance is established. Such means may, for example, be projections and recesses, latching or locking elements and/or abutments associated with one another. It may also be advantageous when the object holder and/or the reagent holder has means which can bring about the detachable connection.

By preventing liquid from passing between the channels during the analysis, it is advantageously possible to simultaneously analyse next to one another several samples on one object holder in the various channels, without there being any risk that the liquids of adjacent samples mix with one another during the incubation.

The adhesive surfaces may be arranged on the object holder surface such that they are planar with respect to it or such that they are flush with respect to it. Alternatively, grooves, elongate recesses or steps extending in parallel from one longitudinal end of the adhesive surfaces to the other may be provided between adjacent adhesive surfaces. This achieves, in an advantageous manner, the effect that the individual adhesive surfaces are offset or contrasted from one another and are each arranged on dedicated, separate elongate projections, i.e., for example, are effectively arranged raised on the surface of the object holder.

It is preferred that the channels of the reagent holder extend in elongate projections disposed on the surface of the reagent holder, wherein the projections of adjacent channels are separated from each other. For example, the individual projections—and hence the channels—may be offset or separated by recesses extending in parallel to the channels and between them from one longitudinal end of the channels to the other, or by a specific step-like profile.

In a preferred configuration, the lateral edges or boundaries of the channels are tapered at the top or provided with a sharp edge, and, in the connected state of object holder and reagent holder, the liquid is prevented from laterally escaping from the channels. This can be achieved, in combination with the tapered edges or boundaries, for example, by virtue of the distance of the edges or boundaries from the adhesive surfaces of the object holder being so small that the liquid is held in the intended position, preventing lateral escape, by adhesive forces from above and below. There is effectively a "capillary with slits on both sides", from which air can escape laterally, but not the liquid.

In a preferred embodiment, the interior surfaces of the channels are provided with a pattern or profile for conducting or guiding the liquid within the channels in the longitudinal direction. Such a pattern or profile may comprise, for example, a groove extending in the longitudinal direction in the bottom of the channel.

It is preferred that for increasing the reservoir function for the liquid with the purpose of leak protection the channels of the reagent holder extend in length beyond the longitudinal ends of the adhesive surfaces of the object holder. In other words, the channels are longer than the adhesive surfaces, and, in the connected state of object holder and reagent holder, the channels protrude beyond the adhesive surfaces at one end or preferably at both ends. In this regard, it may be particularly advantageous when the edges or boundaries of the channels extend upwards or are elevated as compared to the remainder of the channel, in these portions extending beyond the adhesive surfaces in order to form a cup-shaped reservoir that receives excess liquid.

The channels of the reagent holder may advantageously be hydrophilized, in order that the liquid can be introduced more easily into the channels. To this end, hydrophilic substances which do not disrupt the reaction which follows later are preferably introduced into the channels.

In a preferred configuration, around each adhesive surface of the object holder is provided a circumferential border that projects with respect to the adhesive surface. This border may be part of the adhesive surface and form the border thereof, or may be arranged outside the adhesive surface. It is advantageous when the dimensions of the border are such that it projects beyond solid phase substrates having reaction partners bound thereon for reactants dissolved in the channel liquid and to be secured to the adhesive surfaces for analysis, and preferably projects to just such a minor degree that no direct mechanical pressure is exerted on the solid phase substrate in the course of later evaluation through a cover slip placed onto the object holder. In any case, the border then prevents a disadvantageous leakage of mounting medium.

The object holder and the reagent holder are preferably constructed such that, in the connected state of the object holder and the reagent holder, the adhesive surfaces are immersed into the channels, lie at the height of the channel edge or boundary in the contact area or lie above the channel edge or boundary, and liquid present in the channels, before making contact with the adhesive surfaces or during contact, bulges out or forms a dome beyond the channel edge or boundary.

For reliable identification of the object holder in microscope viewing and for reliable assignment to the reagent holders at the beginning of the incubation, the object holders and the reagent holders can advantageously be provided with machine-readable codes.

In an advantageous configuration, baffles or obstacles are provided on the surface or inner surface of the channels. As will be described in the following, the object holder and the reagent holder in the connected state are preferably moved during the analysis or the incubation in such a manner that the liquid in the channels moves alternately back and forth in the longitudinal direction of the channels. As it does so, it flows over the baffles or obstacles, and at these turbulence, or vortices or swirls, is formed in the liquid, which ensures better mixing of the liquid.

During the analysis, solid phase substrates or solid phases having reaction partners for reactants dissolved in the channel liquid bound thereto are preferably arranged on the adhesive surfaces. These solid phase substrates may be arranged in the course of preparation of the object holders or not until immediately before the analysis. The solid phase substrates preferably comprise biological material that is selected from: a) thin sections of biological tissue, b) cell smears of grown cells or united cell structures, c) bacteria smears, d) viruses, protozoa and parasites, e) antigen drops applied in solution, dried or coupled, f) other antigens coupled to a surface and/or g) arbitrary nucleotide sequences.

Such a device can be used advantageously in a method for performing immunological, histochemical and cytochemical, molecular biological, enzymological, clinical-chemical and other analyses, wherein the object holder is connected to the reagent holder in the above-described manner such that the elongate adhesive surfaces each face or are disposed opposite a channel, liquid having reactants dissolved therein is introduced into the channels such that solid phase substrates having reaction partners bound thereto and being disposed on the adhesive surfaces come into contact with the liquid, and the object holder and the reagent holder are moved together in such a manner that the liquid alternately moves into the two longitudinal directions of the channels. After reaction partners and reactants have been incubated in this way, there is a subsequent analysis or evaluation as to whether—and if appropriate to what extent—a reaction has taken place between them.

The movement is preferably performed or the object holder and the reagent holder are preferably configured, such that, in the channels, the liquid of the analysis preparation during the reaction times and the washing liquid during the washing cycles passes or flows tangentially under the adhesive surfaces.

In a preferred configuration of the method, a continuous mixing of each individual analysis preparation, i.e. of the liquid in one channel, during the above movement, is achieved by periodically pivoting the reagent holder together with the object holder lying thereon in the longitudinal direction of the channels sufficiently far from the horizontal that the liquid flows back and forth in the longitudinal direction of the channels and, for example, between the ends of the channels.

It is preferred that, in the above movement, mixing—preferably continuous and complete—of the liquid in each channel is achieved by virtue of the volume of liquid moved in each half cycle from one longitudinal end of the reagent holder channels to the other being larger than the liquid volume under the adhesive surfaces. As a result, the liquid at both ends of each channel is included in the mixing or the permanent exchange.

It is also advantageous when the capacity of the channels is matched or adapted to the volume required for the particular analyses by defining the channel depth.

In the context of the method, it is possible in an advantageous manner to use one solid phase substrate per analysis preparation (single tests) or to use a plurality of solid phase substrates per analysis preparation (mosaic test).

The method can be used for the determination of antibodies in the diagnosis of autoimmune or infection disorders, allergies and tumours, which may preferably be: a) autoantibodies, b) antibodies against infection pathogens: bacteria, viruses, protozoa, yeasts and parasites, c) allergen-specific antibodies of the immunoglobulin classes IgE and IgG, d) antibodies against tumour antigens.

The antibodies can be examined advantageously a) by the technique of direct or indirect immunofluorescence, b) by the immunoblotting technique, including by use of blot membrane-based microarrays, or c) by the luminescence technique.

In addition, the method can be utilized in an advantageous manner using the invention for genotyping of patient samples or other samples with the aid of microarrays.

The method can preferably be performed automatically or semiautomatically. In this case, preferably, (a) the number of reagent holders intended for the tests is placed at a defined position on a swivel table, (b) the corresponding type and number of object holders according to the incubation protocol is placed onto the reagent holders in accordance with the analysis, c) suitable sample dilutions are prepared and introduced into the intended channels of the reagent holder, d) depending on the protocol, one or more incubation steps are carried out, in the course of which the swivel table is set in motion and effective mixing is brought about in the individual preparations, e) wash cycles are inserted between the individual incubation steps, in the course of which the washing liquid is introduced on one side of the channels and sucked out at the other, and during which it is not necessary to remove the object holders from the reagent holders, and f) the results of the particular test variant are evaluated correspondingly. The inventive device is preferably adapted for automatic or semiautomatic use.

Exemplary embodiments of the invention are explained in detail hereinafter with reference to the figures.

Figure 1:
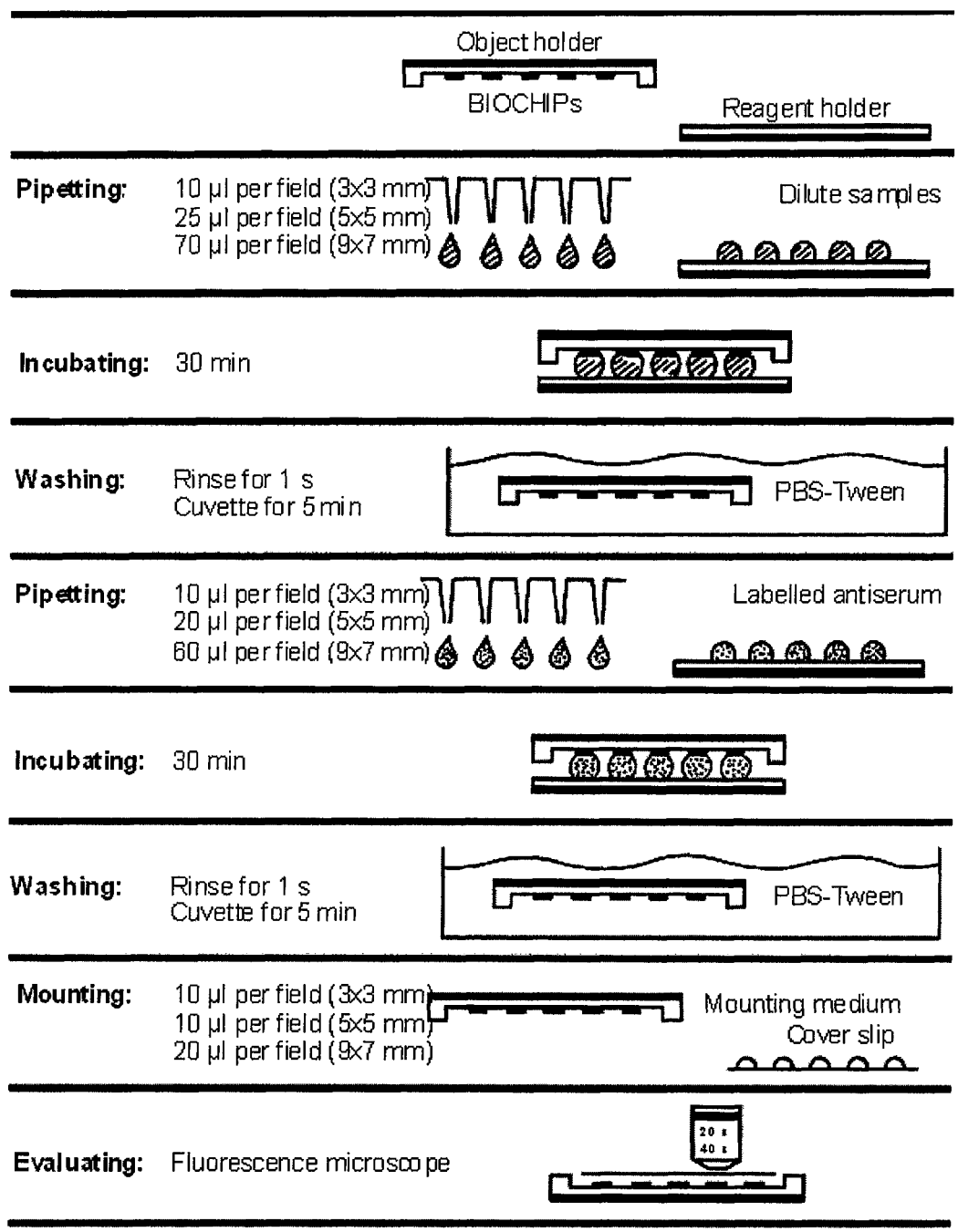
FIG. 1 is a schematic diagram of the "indirect immunofluorescence test" for detecting antibodies in patient serum according to the prior art.
Figure 2:
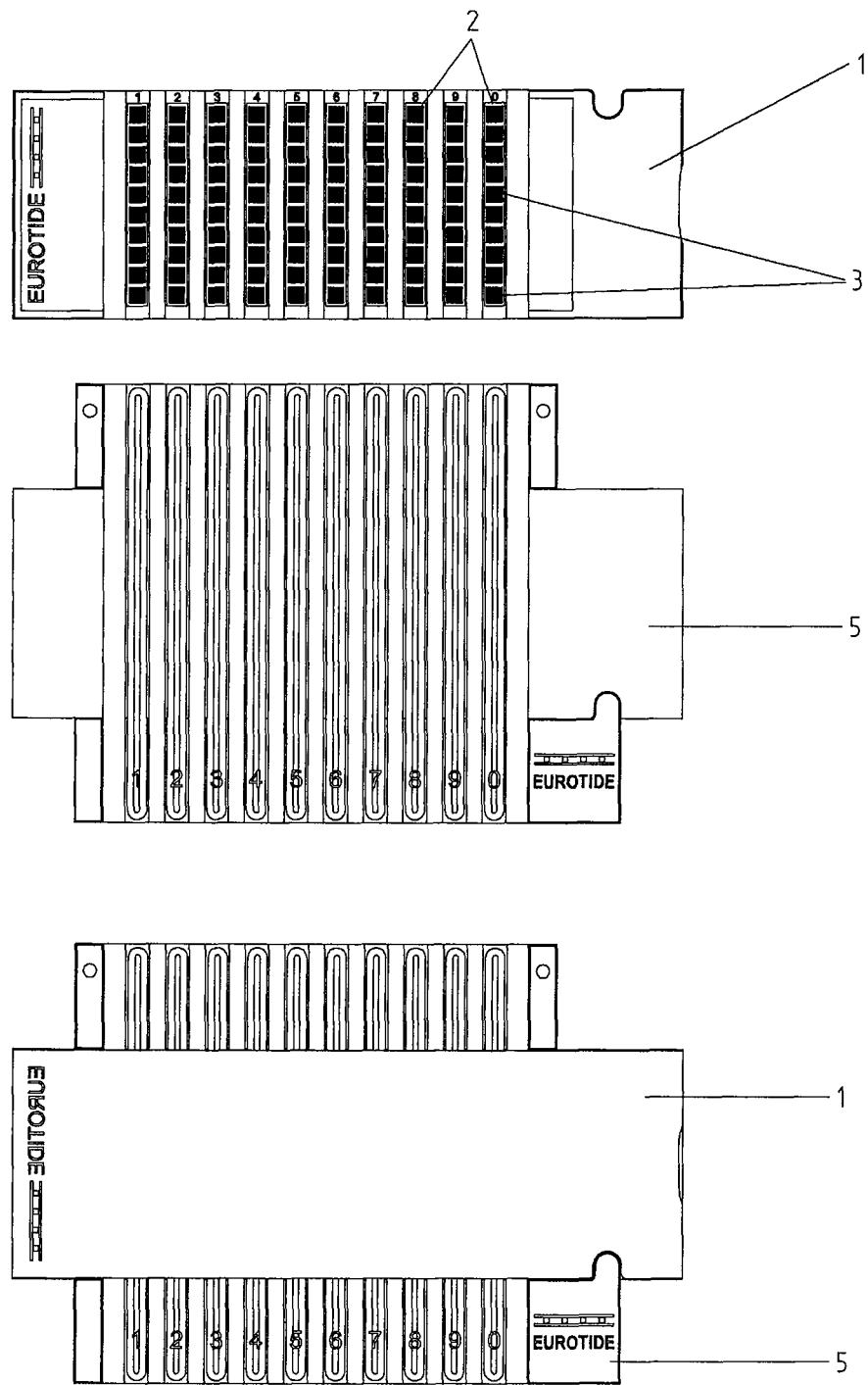
FIG. 2 shows an exemplary embodiment of the object holder and the reagent holder according to the invention.
Figure 3:
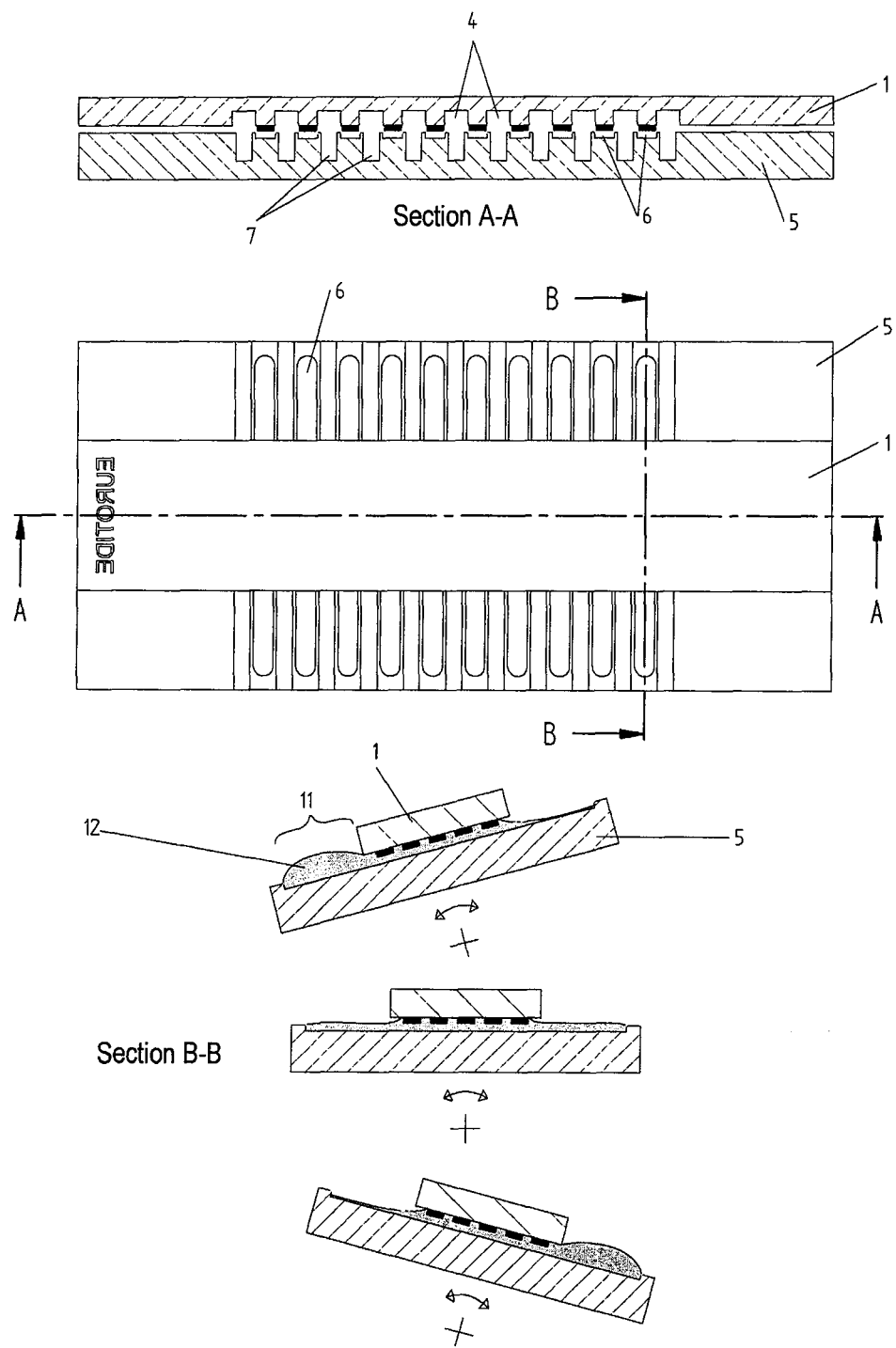
FIG. 3 shows further details of the exemplary embodiment according to FIG. 2.
Figure 4:
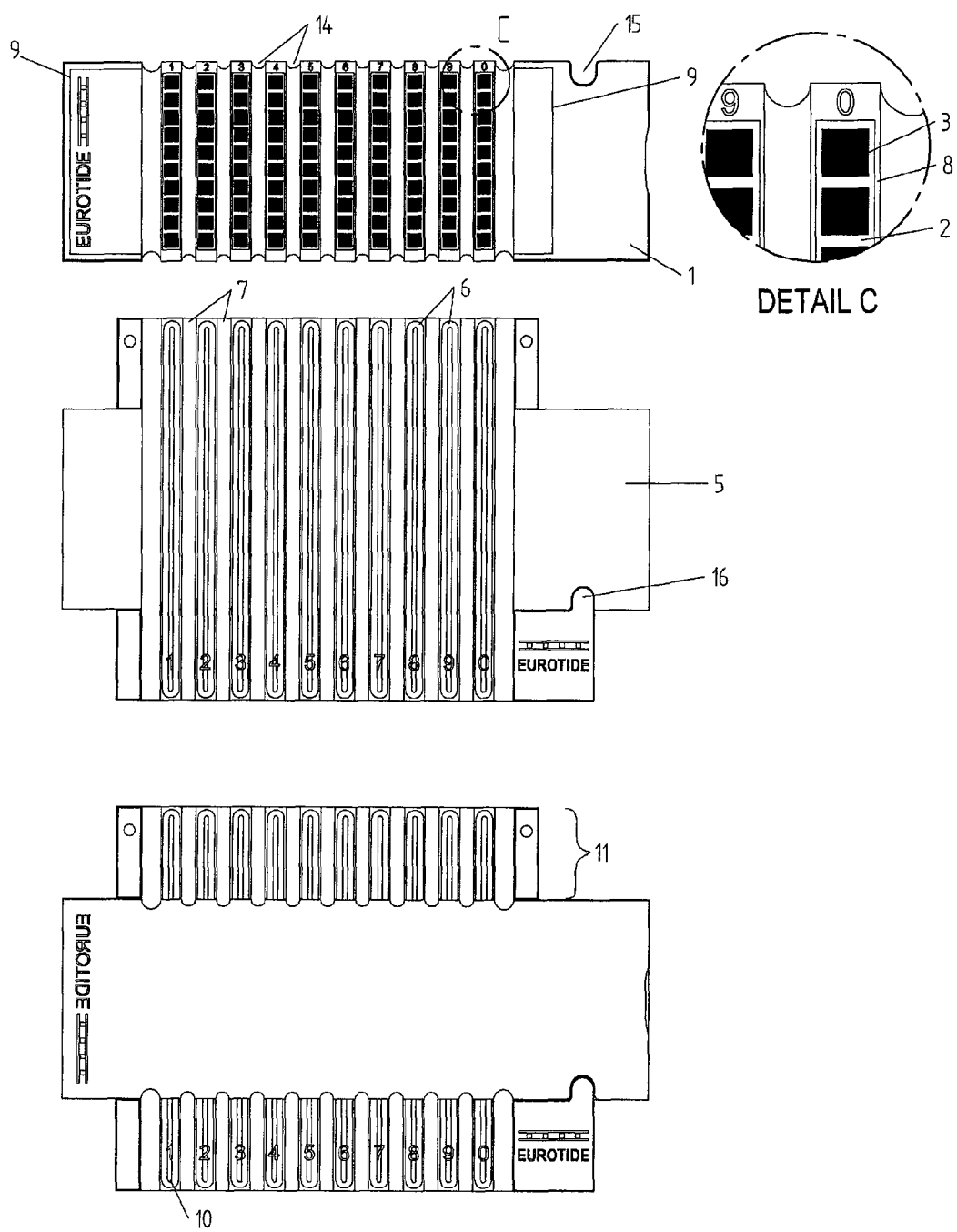
FIG. 4 shows a further exemplary embodiment of the object holder and the reagent holder according to the invention.
Figure 5:
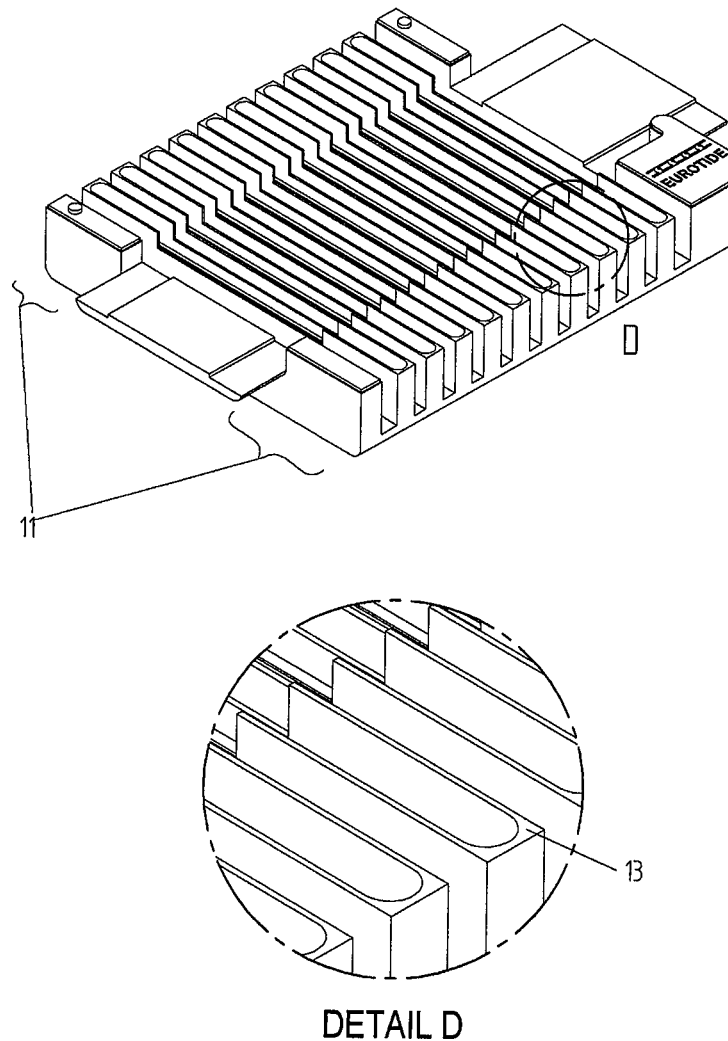
FIG. 5 shows a further exemplary embodiment of the reagent holder according to the invention.

Object holders (1) with one or more elongate adhesive surfaces (2) are provided, to which the solid phase substrates (3) are secured. Each individual adhesive surface (1) may lie planar in the object holder surface, or projects in preferred versions of the invention, separated from the adjacent adhesive surfaces by grooves (4) which run parallel from one longitudinal end of the adhesive surfaces to the other, for delimitation of adjacent reaction preparations from one another. For the incubation, the object holders, with the adhesive surfaces facing downward, are placed onto reagent holders (5) having elongate channels (6) and combined with them temporarily to form a "block". The channels are opposite the adhesive surfaces of the object holders in an exactly defined position and are filled at a given time with the sample liquid or the liquid reagent. They project upward (in particular embodiments in the form of steps) and are offset toward the sides by a specific profile. For instance, the reagent holder may, in addition to the channels, have recesses (7) which run in parallel from one longitudinal end to the other, for delimitation of adjacent reaction preparations from one another. The liquid of the channels is raised towards the adhesive surfaces of the object holders, such that a "capillary slotted at both sides" is formed, from which air can escape, but the liquid is retained in the intended position by adhesive forces from below and above. The edges or boundaries of the channels may be tapered at the top or provided with a sharp edge, in order to prevent the liquid from escaping to the sides. In particular embodiments, the liquid can flow into the capillary at the longitudinal ends of the adhesive surfaces from a bulge of the channel, or leave it therefrom.

The object holders may be placed in the position envisaged for the incubation already before the channels are filled with the liquid, or the liquid is already introduced into the channels before, and the object holders are only placed on them thereafter; in this case, all reactions start simultaneously when the object holder is placed on. The geometry of each block is adapted such that the solid phase substrates come into contact with the liquid held by the channels. In some embodiments, the adhesive fields are immersed into the channels for this purpose; in other embodiments, the adhesive fields are at the height of the channel boundary; in others again, they are higher, and the liquid forms a dome above the channel boundary. Reagent holders with different channel depths are produced, guided by the volume required for the particular analyses. It is equally possible to adapt the width of the adhesive surfaces and of the channels to the requirements.

The combined structure composed of object holder and reagent holder (block) can now be tilted rhythmically by seesaw or rocking motions with any frequency, in such a way that the liquid flows from one longitudinal end of the adhesive surfaces and channels to the other, and then flows back again. At the end of the incubation, the object holders are removed from the reagent holders and the reactions are evaluated. In the case of the indirect immunofluorescence test, mounting medium is contacted with the antigen substrates of the adhesive surfaces and one cover slip per object holder is placed on, then viewed under the microscope.

Each adhesive surface may have a circumferentially extending border (8) which only slightly projects beyond the substrates, but fulfils three important functions: firstly, the boundary facilitates the positioning of the substrate-bearing glass fragments (biochips), which, for example, can no longer as easily slip during adhesive bonding. Secondly, the boundary protects the substrates: the cover slip placed on at the end is kept away from the tissue sections or cells at a small defined distance, and can thus damage them to a lesser degree, which is often the case in conventional techniques where the cover slip directly adjoins the biological material covered with mounting medium. And thirdly, the mounting medium is held firmly between adhesive surfaces and cover slip and cannot escape: the substrates do not dry out, which would render them unusable, and the mechanical stage of the microscope is not contaminated. By means of the circumferential boundary (8) the cover slip is only raised to such an extent that the working distance of the standard microscope lenses from the front lens to the plane of the tissue sections or cells is not exceeded. The surface of the object holders may be provided with recesses (outer edges of the recesses: 9), into which the cover slip can latch, in order that it does not slip to the side in the course of microscope viewing.

In comparison with the already cited EP 0 018 435, in which both object holder and reagent holder require hydrophilic fields in a hydrophobic environment for the positioning of the liquid with respect to the solid phase substrate, a hydrophilic/hydrophobic coating of the object holders or of the reagent holders is not necessary in the present invention. However, it has been found to be useful to hydrophilize the channels of the reagent holders, in order that the liquid can be introduced more easily; this can be achieved, for example, by spray application of hydrophilic substances (which do not interfere with the reaction which follows later), which can optionally be allowed to partially dry. The channels may be equipped with suitable profiles or patterns for guiding the liquid, for example with a flute (10) or several flutes at the bottom of the channel, in order to favourably influence the flow behaviour in the course of filling with sample liquid or reagents and during the seesaw or rocking operation. To promote convection and hence to accelerate the mixing operation, baffles or obstacles may also be incorporated into the surface of the channels, at which baffles or obstacles turbulence forms when liquid flows over them.

The channels preferably possess, at both longitudinal ends, reservoirs for the liquid—they are, for example, configured to be longer (11) than the adhesive surfaces of the object holders. The liquid then flows beyond the end of the adhesive surfaces (12) in the course of the seesaw or rocking motions, and the desired mixing of the sample during the overall incubation becomes even more efficient, especially when the liquid volume of the channels in the proportion which projects beyond the object holders at both ends is designed to be larger on each side than the volume in between, in the region of the adhesive surfaces. The protruding section of the channels additionally serves as a reservoir for accommodating an excess of liquid, in order to safeguard the system from faults resulting from inaccurate pipetting. Also, at this position, sample, reagent and washing liquids are introduced and sucked out, while the object holders are placed on the reagent holders. The invention is therefore particularly suitable, as compared to the entire state of the art, for the automatic processing of large analysis series. It enables, inter alia, the preparations to be washed efficiently after each incubation step, without removing the object holders: washing liquid is added at one longitudinal end, and is sucked out simultaneously at the other. In the course of this, the liquid flows tangentially past the solid phase substrates, which is particularly effective and both shortens the wash cycle and saves large volumes of wash liquid. The washing can be effected in intervals, or else continuously. During the washing in a continuous process, the blocks composed of reagent holders and object holders are tilted predominantly at an oblique angle, in or against the flow direction.

To date, it has been customary in the case of manual performance of the indirect immunofluorescence test to rinse the samples or reagents off the object holders with a copious flush of washing liquid, then the object holders are placed successively into two or three cuvettes with fresh washing liquid in each case, then they are taken out and dried around the reaction fields and on the backside, and reagents or mounting medium are finally manually applied dropwise. The object holders of the present invention need no longer be washed in their entirety and come into contact with potentially infectious liquid only in the region of their adhesive surfaces. And a cover slip is finally placed onto the adhesive surfaces, such that there is barely any risk of infection from the object holders in the course of microscope viewing.

Where the channels of the reagent holders project beyond the object holders (11), the boundaries thereof may extend upwards, in order to form, so to speak, a "cup" (13), for increasing the reservoir function at the ends and for preventing liquid from escaping and possibly even passing over to the next reaction preparation. As a precautionary measure with the same aim, indents (14) may also be provided between the adhesive surfaces at the object holder boundary. Furthermore, notches or projections (15), that correspond with respective counterparts (16) on the reagent holder, may also be provided outside the region of the adhesive surfaces on the object holders. This ensures that the object holders are placed on in the correct orientation and alignment. At the ends of the object holders, a code may be provided, on the top or bottom, for reliable identification when the object holders are positioned in the reagent holders at the start of the incubation or during viewing with a microscope. On the underside of the object holders may be provided planar thin strips on which the object holders slide in the course of microscope viewing, in which case they do not remain adhering on the mechanical stage if it is ever contaminated by oil or mounting medium of an object holder of the earlier state of the art. The object holders may be bevelled by a few degrees at the ends on the underside: when a small pressure is exerted there with the finger from above, the object holders can tilt and rise slightly from the laboratory bench or from the mechanical stage of the microscope.

The reactions of indirect immunofluorescence are found to be remarkably reproducible with the tissue sections or cell substrates incubated in accordance with the invention, completely in contrast to the conventional technique: in the case of a conventional object holder, a more or less round droplet lies on top of the substrate, for example a tissue section. In the middle of the field, the droplet is often higher than on the outside, in which case stronger reactions are observed in the middle since more antibodies are present here. Sometimes, however, the converse is found: where the droplet projects beyond the edge of the tissue section, additional reaction partners are available to the antigens from the outside. It is often possible to observe a further, serious effect: owing to the greater curvature of the surface at the edge of the droplet, the liquid evaporates significantly more rapidly there than in the middle; liquid flows continuously outwards, and a considerable concentration gradient of the antibodies develops—in that case, the edge of the tissue section reacts significantly stronger than the middle, by means of which antibody concentrations which are up to ten times too high are in some cases simulated. (This phenomenon can also be observed at any time in everyday life: on a smooth surface, a dried drop of coffee gives rise to a spot which is quite light on the inside and almost black at the edge.) In the case of tissue sections incubated in accordance with the invention, the histological structures at each point in a preparation show reactions of equal intensity. This advance was achieved by virtue of the reactants in the liquid being permanently mixed efficiently during the incubations—a particular strength of this invention, and one of the prerequisites for a standardisation of the immunofluorescence diagnostics.

Owing to the forced convection of the dissolved reaction partners and the continuous complete mixing of each individual analysis preparation, significantly stronger signals are additionally obtained in the present invention compared to a system at rest, because the maximum concentration of the reactants present in the liquid is always adjacent to the solid phase substrate, and even those reactants of the liquid, for which contact would not have been possible solely through diffusion in the course of incubation owing to the excessively long distance, come into contact with the reaction partners of the solid phase substrate. Finally, in the case of incubation in accordance with the invention, the saturation limit of the reactions is reached more rapidly than in the prior art, and the incubation time can therefore be shortened by one third, for example, for the indirect immunofluorescence.

EXAMPLES

One of the most important applications for the new invention is the serological diagnosis of antibodies by indirect immunofluorescence in laboratory medicine. The new method and the corresponding devices are also suitable, however, for performing many other immunological, histochemical and cytochemical, molecular biological, enzymological, clinical-chemical and other analyses, for tests using immunoblots, microarrays, or fluorometric and luminometric and other analysis methods, for example in medical laboratory diagnostics, in which reaction partners bound to a solid phase are incubated with reactants dissolved in liquids. The same applies for the direct immunofluorescence.

Example 1

Detection of Autoantibodies Against Granulocytes by Indirect Immunofluorescence in the Diagnosis of Wegener's Granulomatosis For single analyses, each adhesive surface of an object holder is provided with one substrate. For this purpose, in this case, isolated granulocytes are streaked on a cover slip and fixed in 96% ethanol at room temperature for 10 minutes. Thereafter, the cover slip is divided into 1×1 millimeter-size fragments with the aid of a glazier's diamond. A respective one of these fragments is adhesively bonded to a respective one of ten adhesive surfaces of the object holder (the adhesive is present between the adhesive surface and the underside of the biochip; the granulocytes are exposed at the surface). The object holder, with the biochips facing downwards, is placed onto a reagent holder having ten channels disposed opposite the adhesive surfaces. The object holder is 26 millimeters in width, and the adhesive surfaces are 24 millimeters in length. The channels protrude by 10 millimeters at each of the two longitudinal ends of the adhesive surfaces.

100 microliters of serum from ten different patients diluted 1:10 in PBS (an aqueous physiological saline solution buffered to pH 7.4 with phosphate) are now introduced manually with a pipette into a respective one of the ten channels. The dimensions of the channels are such that the liquid now comes into contact with the granulocytes. The reagent holder, together with the object holder which lies thereon, is then tilted periodically from the horizontal by 30° in the longitudinal direction of the channels, such that the liquid flows back and forth from one end to the other, with a cycle time of 15 seconds per cycle. The volume in the region of the adhesive surfaces is 20 microliters in each case; the volume moved in each half cycle is designed so as to be significantly greater, 30 microliters here, as a result of which the liquid at the two ends of the channels of each individual test preparation is included in the permanent exchange, and there is vigorous and rapid permanent mixing of the entire preparation of each sample. During the incubations, the block composed of reagent holder and object holder is covered with a hood, in order that the liquid does not evaporate too rapidly and the analysis preparations do not dry out.

After 30 minutes, the serum dilution is sucked out from one end of the channels, and PBS is pipetted in from (preferably but not exclusively) the other end for washing—a total of 10 milliliters per channel within 5 minutes. The channels are then sucked empty, and 100 microliters of a suitable dilution of a fluorescein-labelled antihuman immunoglobulin from goats are introduced (many other antibody sources or antibody-like reactants are conceivable here, but also many other labelling substances). In this process, the reagent again comes into contact with the adhesive surfaces and the antigen substrates fixed thereon. The block composed of reagent holder and object holder is seesawed or rocked for a further half hour, then washed again in the same way. Finally, the channels are sucked empty again, the object holder is removed from the reagent holder, 15 microliters of mounting medium (1:10 glycerol buffered to pH 8.4 with PBS, with addition of 0.1% sodium azide and 2% 1,4-diazabicyclo[2.2.2]octane as an antibleaching agent) are applied dropwise to each of the adhesive surfaces, and a cover slip is placed on, which latches in a corresponding recess at the borders of the object holder. The reactions are assessed under the fluorescence microscope.

Example 2

Detection of Autoantibodies Against Cell Nuclei, Mitochondria and Smooth Muscles by Indirect Immunofluorescence in the Diagnosis of Various Rheumatic Disorders Glass fragments (biochips) coated similarly to the first example are adhesively bonded to each of ten adhesive surfaces of an object holder according to the invention (for example with the standard measures of 76×26 millimeters), except here as a "mosaic", with the following substrates: acetone-fixed human epithelial cells from the cell culture, ethanol-fixed smears of the haemoflagellate *Crithidia luciliae*, unfixed frozen sections of the following rat organs: liver, kidney, stomach, and in addition biochips coated over the surface or at particular points (according to Proost et al. [7]) with the following single antigens: double-stranded DNA, histone H1, the further cell nucleus antigens Sm, RNP, SS-A, SS-B, Scl-70 and nucleosomes, and with the cytoplasmic antigen Jo-1—altogether with 15 different antigen substrates per adhesive surface. Incubation and evaluation are effected in the same way as in example 1, for the ten patients of the object holder in parallel. At the end of the test, it is found whether or not one or more from a spectrum of at least 15 different autoantibodies is present in the serum of each of these patients. The arrangement of the substrates on the adhesive surfaces and the incubation in cooperation with the channels of the reagent holder allows this multitude of parameters to be performed in parallel for ten patients; 150 single analyses are on one single object holder! Since the liquid cannot flow between the adjacent samples, reactions unintendedly crossing each other and corresponding misdiagnoses are virtually ruled out.

Every sophisticated medical laboratory has an interest in being able to test autoantibody profiles. There are many clinical problems for which this is advisable in terms of differential diagnosis: on the one hand, in the case of some clinical syndromes, several autoimmune disorders are respectively possible (in the case of nephritis (kidney inflammation), for example, a Goodpasture's syndrome, the Wegener's granulomatosis, a systemic lupus erythematosis or a rapidly progressive glomerulonephritis); on the other hand, several autoantibodies may be correlated with a particular autoimmune disorder (with a primary biliary liver cirrhosis, for instance, antibodies against mitochondria or against nuclear dots, gp210 and PML; with a systemic lupus erythematosis, antibodies against nDNA, Sm, histone, ribosomal P proteins, proliferating cells' nuclear antigen, cardiolipin, beta-2-glycoprotein, etc.; with an autoimmune thyroiditis, antibodies against thyroid peroxidase, thyroglobulin, TSH receptors and parietal cells of the stomach). The present invention is particularly suitable for creating antibody profiles. This is not limited to autoimmune diagnostics; there are many other fields of use, including the screening of monoclonal antibodies (for example against tumour-associated antigens) in fusion supernatants [8], or the infection serology, as an analogous example shows:

Example 3

Parallel Incubation of 50 Object Holders with Ten Adhesive Surfaces Each for the Detection of Human Antibodies Against Bacteria, Viruses, Protozoa, Yeasts and Parasites by Indirect Immunofluorescence—40 Parameters Per Patient The object holders with the solid phase substrates are produced similarly to example 2, except that glass fragments with the following infection antigen substrates are used here: culture cells infected with measles, mumps, rubella and with any other viruses, all sorts of bacteria or fungus smears, frozen sections of Echinococcus larvae, Toxoplasma gondii smears, but likewise surfaces with defined antigens isolated biochemically in more or less pure form, some produced with recombinant techniques. The incubations are supported by a machine which dilutes the patient sera, introduces the serum dilutions and the reagents into the channels of the reagent holder at a given time, and effects the washing procedures in parallel with the aid of comb-type ten-channel pipettes and suction cannulas.

During the incubations and in some cases also during the washing, all blocks composed of reagent holders with their corresponding object holders are tilted rhythmically from one to the other longitudinal end of the "split capillary" and back, in order to ensure the desired convection. The tilting motion is optionally stopped (only) for those blocks in which pipetting or washing operations are just being undertaken. This ensures that the mixing operation need not be interrupted constantly for the entire preparation. It is equally conceivable that the overall device, including the pipetting system, is mounted on a large tilting table, such that even those blocks in which pipetting and washing operations are currently proceeding need not have a break from seesawing or rocking. The mounting is effected (for now still) manually, and the readoff on the microscope (for now still) visually.

Example 4

Testing of Specific IgE or IgG Antibodies with a Blot Membrane-Based Microarray in Allergy Diagnostics In the immunoblotting technique, proteins or other antigens are immobilized on nitrocellulose membranes, nylon membranes or other membranes, which are then incubated successively with patient samples or other samples, enzyme-labelled antibodies and a colour reagent. Positive reactions appear on the membrane strips as coloured precipitates, which are evaluated visually or automatically with scanner or camera systems [9, 10].

3×26 square membrane chips with an edge length of 1 millimeter are adhesively bonded in three parallel rows to each of the ten adhesive surfaces of an object holder according to the present invention. Each membrane chip contains a defined membrane-coupled allergen (birch pollen, wasp venom and so forth). The incubations are effected similarly to the manner in the preceding examples; however, in the second incubation step an enzyme-labelled antihuman IgE antibody is used, wherein the second incubation step is followed by a washing step and an indicator reaction. In the positive case, a dye precipitates on the membrane chip.

On a single object holder of 76 cm×26 cm, one allergy profile with 78 parameters is obtained for each of ten patients. The use according to the present invention of membrane chips is not restricted solely to allergy diagnostics.

Example 5

Genotyping of Patient Samples with the Aid of Microarrays

Several microarrays bearing specific nucleotide sequences, for example five microarrays each having 50 different oligonucleotide spots [11, 12], are each secured to the adhesive surfaces of an object holder according to the present invention. DNA is extracted from the white blood cells of ten patients. By means of multiplex PCR, predetermined target sequences are amplified therefrom and labelled in a genotype-specific manner. For hybridization, they are introduced into the channels of a reagent holder according to the invention and contacted with the microarrays on the adhesive surfaces of the object holders. Finally, the reactions are evaluated with a specific microarray scanner.

Specifically the examination of very small amounts of nucleic acid with microarrays for molecular biology purposes requires that the reactions are clear, reproducible and very sensitive, which is ensured particularly through the permanent efficient mixing of the reaction liquid during the incubation, primarily owing to the forced convection. Here too, the diagnostics benefits from this invention with regard to the short incubation times.

AUTOMATABILITY OF THE INVENTION

To date, the indirect immunofluorescence in laboratory practise is a domain of individual manual processing and visual evaluation. The state of the analysis technology in this field has been unable to provide automation solutions with high sample throughput, for instance for clinical chemistry. The dilemma can be illustrated by two systems available on the market: the company DAS srl (Rome, Italy) offers an automatic incubator (AP16 IF Plus), and likewise the company Menarini srl (Florence, Italy) (Zenit SP Plus). Both systems pipette the incubation solution directly onto the fields of the object holder. Coalescence or flowing together of these liquid droplets from adjacent fields may result in misdiagnoses, particularly when the object holder surface was wetted outside the reaction fields after the first washing step—in the present invention, the adjacent samples, in contrast, are reliably separated from one another. It offers better prerequisites for automation compared to existing systems, in which the pipetting and washing operations must be constantly observed owing to the proneness to error.

In addition, in both instruments, the liquids are pipetted directly onto the fields of the object holders; in the case of poor adjustment, this can lead to damage to the substrates by the cannulas—in the present invention, this is ruled out because the solid phase substrates cannot come into contact with the cannulas: the liquid is introduced into the channels outside the object holders, and the channels are in addition opposite the substrates.

The "AP16 IF Plus" washes each field separately with a two-cannula system. One cannula dispenses a defined volume of washing solution as a droplet onto the field to be washed; the other sucks this droplet up again directly thereafter. This operation is repeated several times. Alternatively, a continuous washing is also provided, i.e. simultaneous dispension and suction for a defined period. Both variants harbour the risk of contact of the cannula with the substrate. Moreover, this system uses an unnecessarily large amount of washing buffer because a large portion of the rinsing liquid merely flows past the substrates and has no contact with them whatsoever—in contrast to the invention, where the entire washing volume is inevitably conducted through a narrow gap directly past the substrates. After each washing step, in the "AP16 IF Plus", a significant residual volume of washing buffer remains on the substrate, one reason being that the suction cannula has to maintain a safety margin from the substrate. As a result of this, the reagent liquid is diluted in an unforeseeable manner, sometimes more, sometimes less, which has an adverse effect on the precision of the analyses.

The washing method of the "Zenit SP Plus" deliberately accepts cross-contaminations: each object holder is present in a compartment of a dish. First, prior to the washing, sample liquid or reagent is sucked away from the reaction fields of each object holder simultaneously with a plurality of cannulas (cannula bar). Subsequently, the entire compartment is filled with washing buffer, such that washing takes place similarly to the manner in a cuvette. (This procedure is hazardous: some high-titre and reactive antibodies are not sufficiently diluted by the first washing filling and can cause false positive reactions in adjacent reaction fields under these circumstances.) Finally, the compartment is sucked empty again with the cannulas. Here too, there is the risk of damage to the tissue sections by the cannulas. Since the entire surface of the object holder comes into contact with washing liquid, more residual moisture remains on the object holder, which promotes in an uncontrollable manner the flowing together of the droplets from adjacent reaction fields, which droplets are applied in the subsequent incubation step (after contact with a solution composed of serum proteins, the hydrophilicity of an object holder coating is lost). Here too, the reagent solution applied in the second step is too greatly diluted by residual washing liquid.

The present invention, in contrast, enables liquid-saving automatic washing with high efficiency and quality, but avoids the abovementioned risks of the two instruments discussed above. The method of arrangement of the solid phase substrates and the incubation thereof in the channels of the reagent holder enables a parallel washing of the fields in strict separation from one another. When the washing solution is fed in and sucked out via the channels of the reagent holder, the cannulas do not come into contact with the tissue sections. Moreover, only the adhesive surfaces, and not the remaining surface area of the object holder, is wetted in the course of washing, which additionally reduces the risk that the liquids from adjacent fields will flow together. The residual volume of washing buffer after suction can be reduced to a minimum owing to the channel form, as a result of which the reagent solution is not diluted unnecessarily and to a different degree from sample to sample, as in the two prior art machines described.

LITERATURE

1. Stöcker W. Vorrichtung zur Durchführung von Mikroanalysen. European Patent EP 0 018 435 and USA U.S. Pat. No. 4,339,241 (1979).
2. Stöcker, W. Verfahren und Vorrichtungen für Untersuchungen an unbeweglich gemachtem biologischem Material. European Patent EP 0 117 262 and USA U.S. Pat. No. 4,647,543 (1983).
3. Stöcker W, Scriba P C. Die Anwendung einer neuen, rationellen Immunfluoreszenztechnik in der klinischen Routinediagnostik. In: Schatz, H., Doniach, D. (Eds.): Autoimmunität bei Schilddrüsenerkrankungen. Georg-Thieme-Verlag Stuttgart 157-174 (1984).
4. Stöcker W. Rationelle Histochemie mit einer neuen Mikroanalysemethode. Acta Histochem Suppl 31: 269-281 (1985).
5. Stöcker W, Otte M, Ulrich S, Normann D, Finkbeiner H, Stöcker K, Jantschek G, Scriba PC. Autoimmunity to pancreatic juice in Crohn's disease. Results of an autoantibody screening in patients with chronic inflammatory bowel diseases. Scand J Gastroenterol Suppl. 139:41-52 (1987).
6. Stöcker W, Rateike M, Morrin M. Verfahren zur Herstellung Festphasen-gebundener Bioreagenzien. European Patent Application PCT/EP/2005/000974 (2005).
7. Proost S, Schlumberger W, Meyer W, Dähnrich C, Müller-Kunert E, Sonnenberg K, Stöcker W. EUROPLUS—Eine BIOCHIP-Kombination aus Gewebeschnitten und Einzelantigenen für die indirekte Immunfluoreszenz: Endomysium/Gliadin, AMA/M2 und Parietalzellen/Intrinsic-Faktor. J Lab Med 20: 670 (1996).
8. Stöcker W, Poschmann A, Seitz C, Heise R, Homof B, Böcker W. Rationelles Screening von Fusionsüberständen zum histochemischen Nachweis monoklonaler Antikörper gegen Tumor-assoziierte und andere Antigene. Vern Dtsch Ges Path 70: 393-395 (1986).
9. Meyer W, Scheper T, Lehmann H, Stocker W. EUROIMMUN Medizinische Labordiagnostika AG. Selbstklebende Blotmembranen. Registered German utility model DE 202 15 268.5 (2003).
10. Meyer W, Scheper T, Stöcker W. EUROIMMUN Medizinische Labordiagnostika AG. Vorrichtung zur Antikörperdiagnose mit kombinierten Membranen. Registered German utility model DE 202 15 270.7 (2003).
11. Pfeiffer T, Gruber R, Kuon W, Plischke H, Kirsch S, Körner D, Zieseniss S, Schattenkirchner M, Stöcker W, Steller U. Diagnostic microarray assay for SNP-typing of the gene encoding the drug metabolising enzyme arylamine N-acetyltransferase 2 (NAT2). Conference handbook for the DECHEMA status seminar about chip technologies 90 (2007).
12. Steller U, Stöcker W. Verfahren zur Erzeugung perfekter Macro- and Microarrays durch Kombinieren vorselektierter beschichteter Festphasen-Fragmente (BMBF). German and European Patent Application (Laid-open specification) DE 10 20006 027 517.9 and PCT/EP2007/004641 or WO2007140889 (2007).

The invention claimed is:

1. A device to perform immunological, histochemical and cytochemical, molecular biological, enzymological, clinical-chemical and other analyses, wherein the device comprises:

an object holder having at least one elongate adhesive surface having one dimension longer than an orthogonal dimension; and a reagent holder having at least one elongate channel having one dimension longer than an orthogonal dimension, each elongate channel configured to receive a respective elongate adhesive surface, wherein the object holder is detachably connectable to the reagent holder in such a manner that each elongate adhesive surface nests between walls of a respective channel, and in case reaction partners bound to a solid phase are disposed on each elongate adhesive surface and reactants dissolved in liquid are present in each channel, the reaction partners and the reactants are in contact, and wherein means are provided for preventing the liquid from passing from one channel to an adjacent channel where more than one channel is present.

2. A device according to claim 1 wherein more than one channel is present and between adjacent adhesive surfaces, grooves or steps extend in parallel from one longitudinal end of the adhesive surfaces to the other.

3. A device according to claim 1 wherein more than one channel is present, the channels of the reagent holder extend in elongate projections disposed on the surface of the reagent holder, and wherein the projections of adjacent channels are separated from each other.

4. A device according to claim 1 wherein a lateral edge of each channel is tapered at the top and, in the connected state of object holder and reagent holder, the liquid is prevented from laterally exiting from each channel.

5. A device according to claim 1 wherein an interior surface within each channel is provided with a patterned groove in the longitudinal direction.

6. A device according to claim 1 wherein each channel of the reagent holder extends in length beyond the longitudinal ends of each respective adhesive surface of the object holder, the extended length being sufficient to contain liquid displaced by the object holder when the object holder is connected to the reagent holder.

7. A device according to claim 6 wherein the edges of each channel extend upwards in a portion of the channel extending beyond each corresponding adhesive surface to form a cup shaped reservoir configured to accommodate excess liquid.

8. A device according to claim 1 wherein around each adhesive surface of the object holder a circumferentially extending border is provided that projects with respect to the adhesive surface.

9. A device according to claim 1 wherein at least one obstacle is provided in the surface of each channel, the at least one obstacle configured to create turbulence when liquid flows over the at least one obstacle.

10. A device according to claim 1 wherein solid phase substrates having reaction partners bound thereto are attached to each adhesive surface.

11. A device according to claim 10 wherein the solid phase substrates has biological material selected from:
a) thin sections of biological tissue,
b) cell smears of grown cells or united cell structures,
c) bacteria smears,
d) viruses, protozoa and parasites,
e) antigen drops applied in solution, dried or coupled,
f) other antigens coupled to a surface, and
g) any nucleotide sequences.

12. A method for performing immunological, histochemical and cytochemical, molecular biological, enzymological, clinical-chemical and other analyses utilizing a device according to claim 1, comprising:
- connecting the object holder to the reagent holder in such a manner that the elongate adhesive surfaces each face a channel,
- introducing liquid having reactants dissolved therein into the channels such that solid phase substrates having reaction partners bound thereto and being disposed on the adhesive surfaces contact the liquid, and
- moving the object holder and the reagent holder together in such a manner that the liquid alternately moves into the two longitudinal directions of the channels.

13. The method according to claim 12, wherein a continuous mixing of each individual analysis preparation is achieved by periodically pivoting the reagent holder together with the object holder lying on it in the longitudinal direction of the channels as far out of the horizontal that the liquid flows back and forth from one end to the other.

14. The method according to claim 12, wherein a mixing of the liquid in each channel is achieved by providing that the volume of liquid moved in each half cycle from one longitudinal end of the reagent holder channels to the other is larger than the liquid volume under the adhesive surfaces, whereby the liquid at both ends of each channel is included in the mixing.

15. The method according to claim 12, wherein the liquid of the analysis preparation during the reaction times and the washing liquid during the washing cycles tangentially passes under the adhesive surfaces.

16. A device, comprising:
- an object holder having at least one elongate adhesive surface the elongate adhesive surface having one dimension longer than an orthogonal dimension; and
- a reagent holder configured to tilt rhythmically about an axis, the reagent holder having at least one channel, the at least one channel configured to prevent liquid contained in the at least one channel from passing out of the at least one channel when the reagent holder is tilted, the reagent holder configured to detachably connect to the object holder such that each elongate adhesive surface is nested between walls of a respective channel and such that a reaction partner bound to a solid phase disposed on an elongate adhesive surface is in contact with a liquid containing a reactant dissolved therein when the reagent holder is connected to the object holder and the reagent holder is tilted.

17. A device according to claim 16 wherein the object holder has a plurality of elongate adhesive surfaces and the reagent holder has a plurality of channels, each elongate adhesive surface having a corresponding channel.

18. A device, comprising:
- an object holder having a plurality of elongate adhesive surfaces, each elongate adhesive surface having one dimension longer than an orthogonal dimension;
- a reagent holder having a plurality of elongate channels, each elongate channel having one dimension longer than an orthogonal dimension, each elongate adhesive surface corresponding to one of the plurality of elongate channels; and
- an connection structure configured to detachably connect the object holder to the reagent holder such that a reaction partner bound to a solid phase disposed on an elongate adhesive surface is in contact with a liquid containing a reactant dissolved therein and such that a capillary is formed between each elongate edge of each channel and a corresponding edge of an aligned elongate adhesive surface.

19. A device according to claim 18 wherein the reagent holder is configured to tilt back and forth in the longitudinal direction of the channels and wherein each capillary is configured to restrict liquid from flowing out of the respective channel and configured to permit air to flow into and out from the respective channel.

* * * * *